US012669494B2

(12) United States Patent
Locklear

(10) Patent No.: US 12,669,494 B2
(45) Date of Patent: Jun. 30, 2026

(54) SULFUR AND AMORPHOUS DITHIAZINE MEASUREMENT

(71) Applicant: CONOCOPHILLIPS COMPANY, Houston, TX (US)

(72) Inventor: Jay Locklear, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 748 days.

(21) Appl. No.: 18/060,838

(22) Filed: Dec. 1, 2022

(65) Prior Publication Data

US 2023/0176031 A1 Jun. 8, 2023

Related U.S. Application Data

(60) Provisional application No. 63/287,457, filed on Dec. 8, 2021.

(51) Int. Cl.

| | |
|---|---|
| ***E21B 49/00*** | (2006.01) |
| ***E21B 49/08*** | (2006.01) |
| ***G01N 33/00*** | (2006.01) |
| ***G01N 33/28*** | (2006.01) |
| *G01N 33/24* | (2006.01) |

(52) U.S. Cl.
CPC ......... *G01N 33/287* (2013.01); *E21B 49/005* (2013.01); *E21B 49/088* (2013.01); *G01N 33/2823* (2013.01)

(58) Field of Classification Search
CPC ........................ G01N 33/287; G01N 33/2823; E21B 49/088; E21B 49/005
See application file for complete search history.

(56) References Cited

U.S. PATENT DOCUMENTS

| | | | |
|---|---|---|---|
| 3,197,396 | A | 7/1965 | Stedman |
| 3,708,421 | A | 1/1973 | Rippie |
| 4,283,270 | A | 8/1981 | Mchale |
| 4,478,512 | A | 10/1984 | Zoltner |
| 4,978,512 | A | 12/1990 | Dillon |
| 5,104,557 | A | 4/1992 | Lindstrom |
| 5,160,413 | A | 11/1992 | Allison |
| 5,199,978 | A | 4/1993 | Poirier et al. |
| 5,585,334 | A | 12/1996 | Shaw |

(Continued)

FOREIGN PATENT DOCUMENTS

| | | | |
|---|---|---|---|
| WO | 2008049188 | A1 | 5/2008 |
| WO | 2018001604 | A1 | 1/2018 |

OTHER PUBLICATIONS

Pineiro. Raman and DFT Study of the H2S Scavenger Reaction of HET-TRZ under Simulated Contactor Tower Conditions. 2021. (Year: 2021).*

(Continued)

*Primary Examiner* — Rebecca M Fritchman
(74) *Attorney, Agent, or Firm* — Boulware & Valoir PLLC

(57) ABSTRACT

The disclosure describes a method to indirectly measure the amount of elemental sulfur or amorphous dithiazine in a reservoir sample by converting them to $H_2S$ gas. The $H_2S$ is captured via caustic cyanide solution and quantified by analytical methods and correspond to the concentration of elemental sulfur or amorphous dithiazine. The method has particular applicability to determine where best to drill and avoid locations of high sulfur.

6 Claims, 4 Drawing Sheets

(56) References Cited

U.S. PATENT DOCUMENTS

| | | | | |
|---|---|---|---|---|
| 5,618,408 | A | 4/1997 | Poirier et al. | |
| 6,808,919 | B2 | 10/2004 | Ranson et al. | |
| 6,939,717 | B2 * | 9/2005 | Jiang | E21B 49/10 436/25 |
| 8,920,568 | B2 | 12/2014 | Taylor | |
| 8,920,586 | B2 | 12/2014 | Poulakis | |
| 9,612,204 | B2 | 4/2017 | Locklear et al. | |
| 10,392,271 | B2 | 8/2019 | Janson et al. | |
| 10,564,142 | B2 | 2/2020 | Oduro | |
| 10,626,334 | B2 | 4/2020 | Bertrand | |
| 11,199,078 | B2 | 12/2021 | Sharma et al. | |
| 2005/0238556 | A1 | 10/2005 | Pakulski et al. | |
| 2008/0308463 | A1 | 12/2008 | Keckler | |
| 2013/0149788 | A1 | 6/2013 | Sacks et al. | |
| 2014/0158876 | A1 * | 6/2014 | Jones | E21B 41/02 166/250.01 |
| 2014/0171721 | A1 | 6/2014 | Bertrand | |
| 2015/0267113 | A1 | 9/2015 | Ramachandran et al. | |
| 2017/0269054 | A1 * | 9/2017 | Horton | G01N 33/287 |
| 2021/0102932 | A1 | 4/2021 | Locklear et al. | |
| 2022/0112433 | A1 | 4/2022 | Locklear et al. | |
| 2022/0112443 | A1 | 4/2022 | Locklear et al. | |

OTHER PUBLICATIONS

International Search Report for PCT/US22/80755 dated Apr. 25, 2023. (Attached).

Taylor, G. N.; Matherly, R. "Use of portable analytical methods to determine the stoichiometry of reaction for hexahydrotriazine-based hydrogen sulfide." Anal Chem (2014) 86, 4879-4882.

Saleh, T. A. "Characterization, determination and elimination technologies for sulfur from petroleum: Toward cleaner fuel and a safe environment." Trends in Environmental Anal. Chem. (2020) vol. 25, e0080.

Long, J. H. "A textbook of elementary analytical chemistry qualitative and volumetric." (1910).

Taylor, G. N.; Matherly, R. Structural elucidation of solid byproduct from the useof 1,3,5-Tris(hydroxyalkyl) hexahydro-s-triazine based hydrogen sulfide scavengers. Industrial &Engineering Chemical Reserach. 2011, 50, 735-740.

Kwasniewski,, M.; Allison, R. B.; Wilcox, W. F.; Sacks, G. .L "Convenient, inexpensive quantification of elemental sulfur by simultaneous in situ reduction and calorimetric detection." Anal. Chim. Acta. 2011, 703 (1), 52-57.

ASTM D2622-16 Standard test method for sulfur in petroleum products by wavelength dispersive X-ray Fluorescence Spectrometry, 2016.

ASTM D5623-19 "Standard test method for sulfur compounds in light petroleum liquids by gas chromatography and sulfur selective detection," 2019.

ASTM D5453-19a "Standard test method for determination of total sulfur in light hydrocarbons, spark ignition engine uel diesel engine fuel, and engine oil by ultraviolet fluorescence," 2019.

ASTM D4292-17 "Standard test method for determination of vibrated bulk density of calcined petroleum coke," 2017.

ASTM D129-18 "Standard test method for sulfur in petroleum products (general high pressure decomposition device method)," 2018.

Supplementary Partial European Search Report for European Application No. EP 22905251 dated Nov. 7, 2025.

Agbroko, O. W., et al. "A comprehensive review of H2S scavenger technologies from Oil and gas stream." ChemBioEng Rev, 4, No. 6, 339-359 (2017).

Chakraborty, S., et al. "Effective removal of hydrogen sulfide and mercaptans in oilfield applications." Paper No. SPE-184589-MS, Paper presented at the SPE International Conference on Oilfield Chemistry, Montgomery, Texas, USA, (2017).

Wylde, J. J., et al. "Formation, chemical characterization, and oxidative dissolution of amorphous polymeric dithiazine (apDTZ) during the use of the H2S scavenger monoethanolamine-triazine." Energy Fuels, 34, 9923-9931 (2020).

* cited by examiner

SULFUR AND AMORPHOUS DITHIAZINE MEASUREMENT

PRIOR RELATED APPLICATIONS

This application claims priority to U.S. Ser. No. 63/287,457, filed Dec. 8, 2021, and incorporated by reference in its entirety for all purposes.

FEDERALLY SPONSORED RESEARCH STATEMENT

Not applicable.

FIELD OF THE DISCLOSURE

The present disclosure generally relates to indirect methods for measurement of elemental sulfur and amorphous dithiazine in unconventional reservoirs and/or petroleum production and processing equipment. These methods have particular applicability when used to track sulfur content in drilling mud and other samples that can be assigned a location in the reservoir and thereby inform the directional drilling process to drill away from higher sulfur areas, thereby reducing sulfur scavenging cost and the cost of producing oil.

BACKGROUND OF THE DISCLOSURE

Hydrogen Sulfide ($H_2S$) is a common problem in unconventional oil and gas reservoirs. It is a toxic, corrosive and extremely flammable gas that can cause wide range of adverse health effects if not handled properly. A process called 'sweetening' is used to remove $H_2S$ gas from the production stream so as to make the produced oil and gas suitable for transport and sale. A common approach to sweeten oil is to use an $H_2S$ scavenger, particularly triazine. The $H_2S$ scavenger subsequently reacts with the $H_2S$ gas converting it to a more non-volatile product, which can be more easily removed from the hydrocarbon stream. However, there is considerable cost associated with sweetening, and it would be advantageous to avoid these costs where possible.

One possible way to reduce the cost and effort associated with $H_2S$ scavenging processes and chemicals is to drill the oil well away from the sour zones. Both water-based and oil-based drilling fluids typically contain $H_2S$ scavengers. If the amount of $H_2S$ scavenger in drilling fluids is known, and the by-products of $H_2S$ scavenger reaction are quantified in the drilling mud, the amount of $H_2S$ in the formation can in theory be determined. Thus, by sampling drilling mud during drilling or by drilling test wells, and the like, a drilling plan could be designed such that the production of high $H_2S$ zones is avoided, thus costs associated with pumping $H_2S$ scavengers can be avoided or at least minimized. If certain samples of drilling mud display high $H_2S$, then directional drilling can avoid those locations, and preferably target sweeter crudes.

Concentration of $H_2S$ in a given sample can be measured by monitoring the amount of $H_2S$ scavenger by-product. Commonly used $H_2S$ scavengers are triazines that get converted into dithiazines. Field Asymmetric Ion Mobility Spectrometry (FAIMS) is a known method of monitoring the amount of dithiazine formed during the reaction of conversion of $H_2S$ by triazines. However, the $H_2S$ scavenger chemicals also produce insoluble amorphous dithiazine (a-DTZ) that can deposit on surfaces and confound the results because the FAIMS method can only be used for crystalline dithiazine—the insoluble a-DTZ remains undetected.

Quantifying only the crystalline dithiazine by FAIMS underestimates $H_2S$, and drilling in such a formation would in actuality require larger amounts of $H_2S$ scavenger chemical than anticipated. Thus, a method for determining the accurate amount of a-DTZ is very important, so that all the by-products of $H_2S$ scavenger reaction—crystalline and amorphous dithiazine can be quantified and the amount of $H_2S$ in the crude oil can be determined for proper remediation action. Currently, there are no known methods for the direct determination of a-DTZ.

Another related issue with crude oil is the presence of elemental sulfur. Crude oil containing high amounts of elemental sulfur, is likely to produce copious quantities of $H_2S$ gas during crude distillation process. This release of $H_2S$ during distillation can cause immense safety concerns and can also be detrimental to distillation apparatus and set-up. If it can be known during the drilling process that a crude contains high levels of elemental sulfur and those levels can be measured, appropriate safety precautions and other measures can be taken during processing of crude oil. Measures such as constant monitoring the temperature during distillation, distilling smaller amounts at a given time, attaching appropriate $H_2S$ gas trapping device to the distillation apparatus, etc., can be planned for safe processing of high sulfur containing crudes. In addition, the high sulfur zones could potentially be avoided where the deposits are localized.

There are several methods to measure the concentration of elemental sulfur. Generally, these approaches are classified as either direct or indirect methods of sulfur measurement. In direct methods, elemental sulfur is measured by appropriate instrumentation by sulfur chemiluminescence detection, mass spectrometry or high-performance liquid chromatography with UV-VIS detection (HPLC-UV/VIS). Sulfur in petroleum and petroleum products can also be detected using X-ray fluorescence (XRF). Commonly used methods include ASTM D2622 wavelength dispersive XRF (WDXRF), ASTM D4294 energy dispersive XRF (EDXRF) and ASTM D5453 (ultraviolet (UV)-fluorescence). All three methods were found to be equivalent in the 150-500 mg/kg (ppm) sulfur range.

Sulfur in petroleum products and feedstock at very low concentrations (sub-ppm to ppm levels) are measured by hydrogenolysis and calorimetric methods. With regard to low sulfur fuels (gasoline, jet fuel, and diesel) ASTM D5453 is a good method, with around a 1 ppm sulfur accuracy.

However, the above methods require bulky and expensive equipment needing special organic solvents and power settings, and thus are not ideal field methods. Measuring elemental sulfur in black oils takes time and is expensive as samples need to be shipped to an appropriate laboratory and then measurements carried out by trained personnel.

Another disadvantage of using the instruments like gas chromatography (GC), and HPLC is that they are usually configured for hydrocarbon analysis, not sulfur analysis as sulfur is not one of the commonly measured elements on the GC. Thus, the instrument must be modified each time sulfur is to be measured in a sample. It is a time-consuming exercise to configure GC for new elements and after detection, configure it back to more commonly used analysis. It is advantageous to prepare sample to "fit" existing instrument configurations to maintain a routine analysis schedule.

In indirect elemental sulfur determination methods, elemental sulfur ($S_8$) is converted to a more readily characterized product via one or more chemical reactions and measuring the amount of the reaction product, and then correlating that with the starting elemental sulfur. For example, one way to detect elemental sulfur in crude oil deposits is to convert elemental sulfur to volatile $H_2S$ gas using appropriate chemical reagents and determining the amount of $H_2S$ gas from the test sample to quantify elemental sulfur.

Thus, what is needed in the art is a method to measure a-DTZ and elemental sulfur. The ideal method would provide sulfur and a-DTZ detection at very low concentrations—ideally <10 mg/L detection limits. Detection method tests should be easy to perform without bulky equipment and should preferably be more sensitive than traditionally used methods like GC, chemiluminescence, mass spectrometry, HPLC, etc.

SUMMARY OF THE DISCLOSURE

Both water-based and oil-based drilling fluids typically contain added $H_2S$ scavenger. One common triazine-based scavenger is 1,3,5-tri-(2-hydroxyethyl)-hexahydro-s-triazine, or MEA-triazine (CAS 4719-04-4), consisting of a triazine ring with three monoethanolamine side groups, as shown in FIG. 1. MEA-triazine offers significant $H_2S$ scavenging capacity. Not only does the triazine ring capture sulfur, but so does the monoethanolamine released during the reaction if $CO_2$ is not present.

During the reaction, MEA-triazine is converted into the two-sulfur-containing dithiazine, illustrated in FIG. 2. The single-sulfur-substituted thiadiazine has an exceedingly short lifetime, while a three-sulfur compound (trithiane) is uncommon. Therefore, dithiazine is the most prevalent scavenging by-product. The dithiazine can be quantified, and its amounts related back to $H_2S$ levels.

In our first attempt to monitor $H_2S$ using monoethanolamine (MEA) triazine, MEA-dithiazine was found at <5 mg/L concentrations in the solids and fluids even though the precursor, MEA triazine concentration in the fluid started at ~1000 mg/L. The loss is not fully explained but may be attributed to the tendency of MEA-dithiazine to polymerize and form amorphous DTZ (a-DZT), which was not detectable in our initial study. See FIG. 3. Thus, any effort to track $H_2S$ in drilling mud must account for losses to a-DZT, and this realization led to the current invention, wherein a-DTZ is reacted stoichiometrically with a reductive mercaptan solution and converted into $H_2S$ gas. This evolved gas is trapped, measured, and correlated to the amount of starting a-DTZ. The amount of a-DTZ measured can then be used to back calculate the exact amount of $H_2S$ scavenger chemicals consumed, and thus relate to the $H_2S$ levels in the drilling mud, providing a more accurate accounting of sulfur in the reservoir.

A similar principle can be applied to determine the amount of elemental sulfur in crude oils. Elemental sulfur can be reacted with the reductive mercaptan solution to produce $H_2S$ gas that can be trapped, measured and correlated to the amount of starting elemental sulfur. By knowing that the crude oil has higher amounts of elemental sulfur, crude oil processing procedures can be modified to include proper safety measures.

The invention thus generally relates to methods to detect a-DTZ and elemental sulfur by reacting them with reductive solution of mercaptan to produce $H_2S$ gas that can be detected and quantified. Preferably, the $H_2S$ is detected by reaction with caustic cyanide solution resulting in production of thiocyanate or isothiocyanate. This thiocyanate and/or isothiocyanate is then measured by commonly known methods in the art, e.g., by ion chromatography, spectrophotometry or colorimetry, and back calculated to determine the amount of a-DTZ or elemental sulfur in the original solution.

The molar amount of thiocyanate and/or isothiocyanate detected may be related to the amount of a-DZT in a ratio that can vary depending on the number of polysulfide inclusions along the polymer back bone, but should be relatively constant for a set of conditions, and are related to the amount of $S_8$ in a 1:8 ratio. Amorphous DTZ reacts stoichiometrically with mercaptans to evolve $H_2S$ gas as shown in the reaction in Eq. 1. Elemental Sulfur reacts with mercaptans to evolve $H_2S$ gas as shown in Eq. 2.

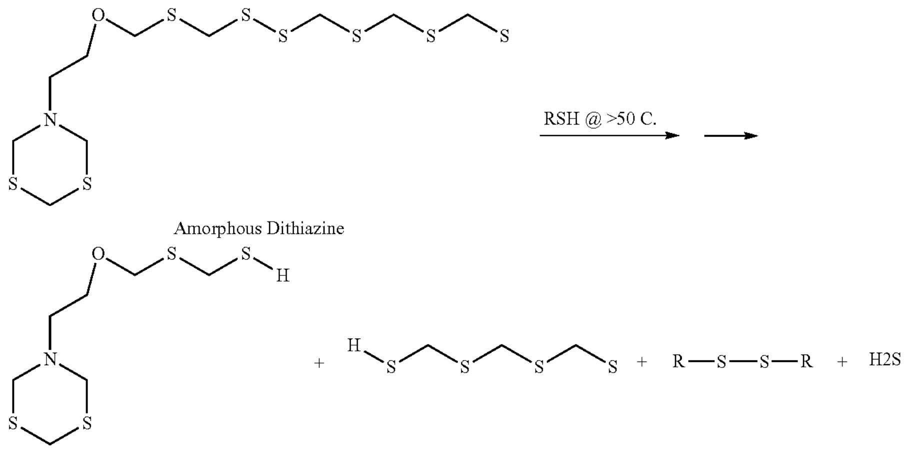

Eq. 1. Reaction of a-DTZ with mercaptans to produce $H_2S$ gas.

$$S_8 + 8\,R{-}SH \longrightarrow 8H_2S + 8\,R{-}S{-}S{-}R$$

Eq. 2. Reaction of elemental Sulfur ($S_8$) with mercaptans to $H_2S$ gas.

In both cases, the samples may require pretreatment by acidification and dilution to eliminate endogenous $H_2S$, which would result in overestimating the $H_2S$ and thus $S_8$.

Thus, pretreatment methods for the samples are also provided in the present disclosure.

If one is interested in quantitating $H_2S$ in drilling mud that contains triazines, any remnant $H_2S$ that fails to be scavenged can be measured as indicated herein in one sample or portion thereof. Another sample or portion of the original sample can then be measured for dithiazine levels, and finally a third sample or portion of the original sample may be assayed for a-DZT levels. In each case, molar amounts are correlated back to the original $H_2S$ levels, and the 3 numbers can be added for total $H_2S$ in the drilling sample.

In more detail, a-DTZ in the drilling mud is reacted with reductive mercaptan solution containing a mercaptan, an amine, an alcohol and optionally a hydrocarbon, to convert a-DZT to $H_2S$ which is then reacted with caustic cyanide to form thiocyanate or isothiocyanate, which is then detected in any known method, typically colorimetrically. Detection of $S_8$ is similar—reacting the $S_8$ with a mercaptan to form $H_2S$, which is then analyzed in the same manner.

The invention includes any one or more of the following embodiments in any combinations(s) thereof:

A method of assaying amorphous DZT (a-DZT) in a reservoir sample, said method comprising: a) obtaining a sample from a reservoir containing MEA or a triazine, or MEA or a triazine being added thereto; b) analyzing said sample or portion thereof to determine an amount of a-DZT therein by treatment with a reductive solution comprising a mercaptan plus an amine plus an alcohol to convert a-DZT to $H_2S$; c) measuring an amount of $H_2S$; and d) calculating an amount of a-DZT in said sample from said amount of $H_2S$.

Any method of assaying amorphous DZT as herein described, wherein said sample is a drilling mud sample obtained while drilling an oil well or a test well or wherein said sample is a core sample.

Any method of assaying amorphous DZT as herein described, wherein $H_2S$ is measured by reaction with caustic cyanide and determining an amount of thiocyanate or isothiocyanate produced.

Any method of assaying amorphous DZT as herein described, wherein thiocyanate or isothiocyanate are determined by reaction with iron or copper plus pyridine and measuring an amount of color produced.

Any method of assaying amorphous DZT as herein described, where said sample is pretreated before step b) to remove any dissolved $H_2S$ in said sample.

A method of avoiding drilling in high $H_2S$ or sour reservoir zones, said method comprising: a) obtaining a plurality of samples, each sample from a known location in a reservoir and containing MEA or a triazine, or MEA or a triazine being added thereto; b) optionally analyzing each of said plurality of samples or portion thereof to determine an first amount of $H_2S$ remaining unreacted with said MEA or triazine (this step may be omitted if excess triazine is used such that the reaction is driven to completion); c) analyzing each of said plurality of samples or portion thereof to determine an amount of dithiazine and correlating said amount of dithiazine to a second amount of $H_2S$; d) analyzing each of said plurality of samples or portion thereof for an amount of a-DZT by treatment with a reductive mercaptan solution to convert a-DZT to $H_2S$ and measuring a third amount of $H_2S$; e) calculating a total amount of $H_2S$ in a sample from a location by adding said first amount, said second amount and said third amount, thereby determining one or more highest $H_2S$ content location(s) in said reservoir; f) changing a direction of drilling of an oil well to avoid said one or more highest $H_2S$ containing location(s); and g) producing oil from said oil well, wherein said oil is less sour or has less $H_2S$ than a method of producing oil from said reservoir without said changing step f.

Any method of avoiding drilling in high $H_2S$ or sour reservoir zones as herein described, wherein said plurality of samples are drilling mud samples or a test well or are core samples.

Any method of avoiding drilling in high $H_2S$ or sour reservoir zones as herein described, wherein said reductive mercaptan solution comprises a mercaptan, an amine and an alcohol.

Any method of avoiding drilling in high $H_2S$ or sour reservoir zones as herein described, wherein $H_2S$ is measured by reaction with caustic cyanide and determining an amount of thiocyanate or isothiocyanate produced.

Any method of avoiding drilling in high $H_2S$ or sour reservoir zones as herein described, wherein thiocyanate or isothiocyanate are determined by reaction with iron or copper plus pyridine and measuring an amount of color produced.

A method of measuring elemental sulfur from a reservoir sample, the method comprising the following steps: a) centrifuging a reservoir sample to remove entrained water if needed; b) removing dissolved $H_2S$ in said sample if needed; c) adding a reducing agent comprising a mercaptan to said sample to convert elemental sulfur to $H_2S$; d) quantitating an amount of $H_2S$; and e) calculating an amount of elemental sulfur in said sample from said amount of $H_2S$. As above, the samples can be divided for these analyses, or sufficient numbers of samples collected from each location, as most convenient.

Any method of measuring elemental sulfur from a reservoir sample as herein described, wherein said removing dissolved $H_2S$ in said sample is by acidification, dilution and refluxing.

Any method of measuring elemental sulfur from a reservoir sample as herein described, wherein $H_2S$ is quantitated by reaction with caustic cyanide to produce thiocyanate and/or isothiocyanate, and thiocyanate and/or isothiocyanate are measured.

Any method of measuring elemental sulfur from a reservoir sample as herein described, wherein thiocyanate and/or isothiocyanate are measured by ion chromatography or colorimetry or spectrophotometry.

Any method of measuring elemental sulfur from a reservoir sample as herein described, wherein determining an amount of elemental sulfur in said sample is done by correlating thiocyanate and/or isothiocyanate to elemental sulfur and calculating an amount of elemental sulfur in said sample.

The mercaptan may be C1-C8 carbon length long, and may also contain a hydroxyl group, and may be selected from methanethiol; ethanethiol; 1-propanethiol; 2-propanethiol; allyl mercaptan; butanethiol; t-butyl mercaptan; pentanethiols; thiophenol; dimercaptosuccinic acid; thioacetic acid; 2-mercaptoethanol; dithiothreitol/dithioerythritol (an epimeric pair); 2-mercaptoindole; furan-2-ylmethanethiol; 3-mercaptopropane-1,2-diol; 3-mercapto-1-propanesulfonic acid; 1-hexadecanethiol; and the like, as well as combinations thereof.

The amines used in the reductive solution may be alkyl amines, alkyl hydroxy amines, amino acids, amino saccharides, diamines, triamines, alkyl benzyl amines, and combinations thereof and may be selected from methylamine, propylamine, monoethanolamine, diethanolamine, i-propanolamine, di-i-propanolamine, tris(2-aminoethyl)amine glucosamine, ethylene diamine, methyldiethanolamine, triethanolamine, dithiothreitol, diethylenetriamine, pyrrolidine, pyrrolidone, triethylamine, 1-methyl-2-pyrrolidinone, N,N-dimethyl-N-(2-hydroxypropyl)amine, N,N,N'-trimethyl-N'-(2-hydroxypropyl)ethylenediamine, N,N,N',N"-tetramethyl-N"-(2)-hydroxypropyl)diethylenetriamine, N,N,N',N",N"'-pentamethyl-N"'-(2-hydroxypropyl)triethylenetetramine, and the like, or combinations thereof.

The alcohols used in the reductive solution may be selected from methanol, ethanol, n-propanol, i-propanol, t-butanol, 1-hexanol, cyclopentanol, cyclohexanol, octanol, and the like, as well as combinations thereof.

Optionally hydrocarbons are added to the reducing agent solution to maintain certain viscosity. The hydrocarbon may be straight chain, branched, cyclic, olefinic, aromatic C5-C10 carbon chain, and chosen from any one of pentane, hexane, octane, decane, cyclohexane, 1-heptene, xylenes, toluene, and combinations thereof.

The heating mantle can heat from 30 to 80° C., depending on the combinations of mercaptan, amine and alcohol used as the reductive solution. For example, for a combination of dithiothreitol, monoethanolamine and cyclohexanol, an appropriate temperature of 50° C. is used. Commonly used temperature ranges are between 45 to 65° C.

Subject to the amount of starting sample used for detection, heating is carried out for about 15-45 minutes to release the $H_2S$ gas. For example, for 0.25-1.0 g of starting sample, heating to about 15-20 minutes at about 50° C. will affect the conversion of the a-DTZ or elemental sulfur in the sample to $H_2S$, which can be detected. For starting amounts between 1.0-3.0 g, heating to about 30-40 minutes at about 50° C. is required.

As used herein, elemental sulfur is typically in the form $S_8$, since S alone is unstable and under normal conditions, sulfur atoms form cyclic octatomic molecules with a chemical formula $S_8$.

The use of the word "a" or "an" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim. The phrase "consisting of" is closed, and excludes all additional elements. The phrase "consisting essentially of" excludes additional material elements, but allows the inclusions of non-material elements that do not substantially change the nature of the invention, such as instructions for use, buffers, and the like. Any claim or claim element introduced with the open transition term "comprising," may also be narrowed to use the phrases "consisting essentially of" or "consisting of," and vice versa. However, the entirety of claim language is not repeated verbatim in the interest of brevity herein.

The following abbreviations are used herein:

| ABBREVIATION | TERM |
|---|---|
| a-DTZ | Amorphous Dithiazine |
| $H_2S$ | Hydrogen Sulfide |
| FAIMS | Field Asymmetric Ion Mobility Spectrometry |
| MEA Triazine | Monoethanolamine Triazine |
| DTT | Dithiothreitol |
| HPLC | High Performance Liquid Chromatography |
| UV-VIS | Ultra Violet-Visible Spectroscopy |
| GC | Gas Chromatography |
| XRF | X-ray Fluorescence |
| WDXRF | Wavelength Dispersive X-ray Fluorescence |
| EDXRF | Energy Dispersive X-ray Fluorescence |

-continued

DETAILED DESCRIPTION

There are several ways to measure elemental sulfur in crude oil and other reservoir samples, and herein we use an indirect method wherein elemental sulfur is converted to $H_2S$ gas using a reductive mercaptan solution.

We also report the only indirect method for the measurement of amorphous DTZ which is a by-product of $H_2S$ scavenger reaction, thus allowing quantitation of total $H_2S$ in drilling mud samples treated with scavenger. Amorphous DTZ also reacts with reductive mercaptan solutions to release $H_2S$ gas. This evolved gas is trapped and quantified to correspond to the a-DTZ or elemental sulfur in the starting sample. See FIG. 1-5 for exemplary reactions.

The $H_2S$ gas produced in the above two reactions then reacts with caustic cyanide solutions to form thiocyanates and/or isothiocyanates. There are a number of analytical methods available for the quantification of thiocyanates and isothiocyanates including spectrophotometric analysis, colorimetry with iron salts, copper-pyridine method, ion chromatography and the like. The amount of thiocyanate and/or isothiocyanates calculated by one of these methods correspond to the amount of $H_2S$ gas released by the reaction of a-DTZ or elemental sulfur with reductive mercaptan solution. This method ensures accurate measurement of a-DTZ or elemental sulfur in the starting sample.

Figure 1:
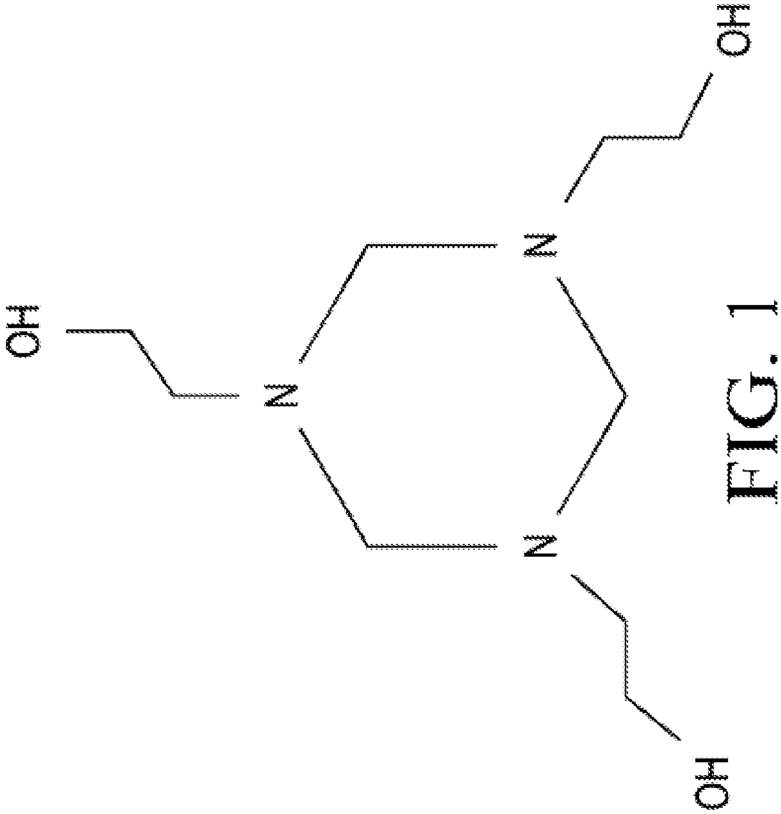
FIG. 1. MEA triazine.
Figure 2:
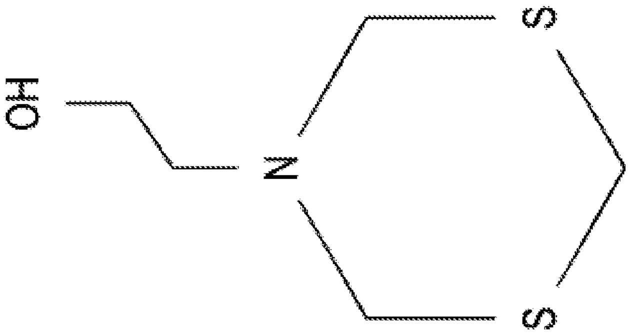
FIG. 2. Dithiazine.
Figure 3:
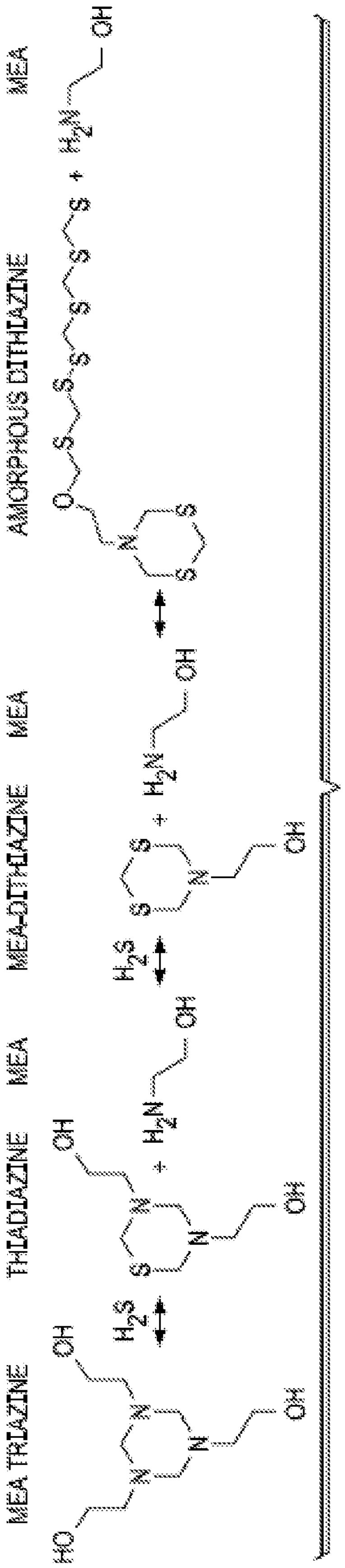
FIG. 3. MEA triazine reaction with $H_2S$ and MEA-dithiazine reaction to a-DTZ.
Figure 4:
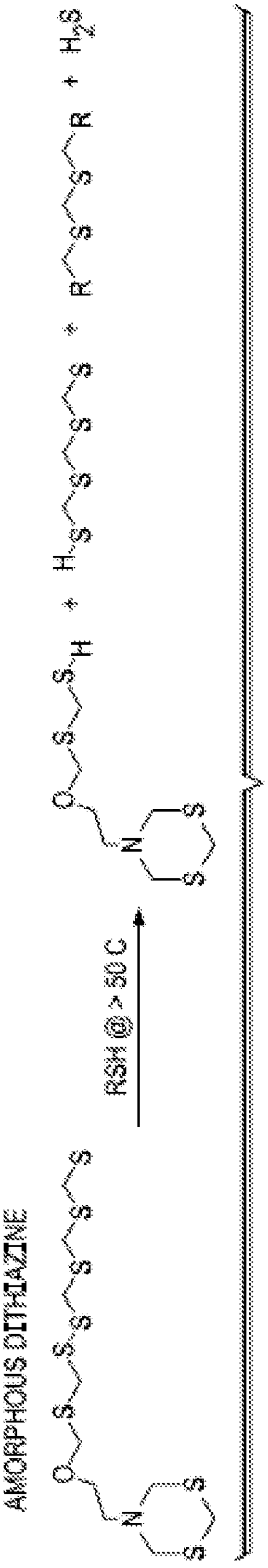
FIG. 4. a-DTZ dissolution reaction.
Figure 5:
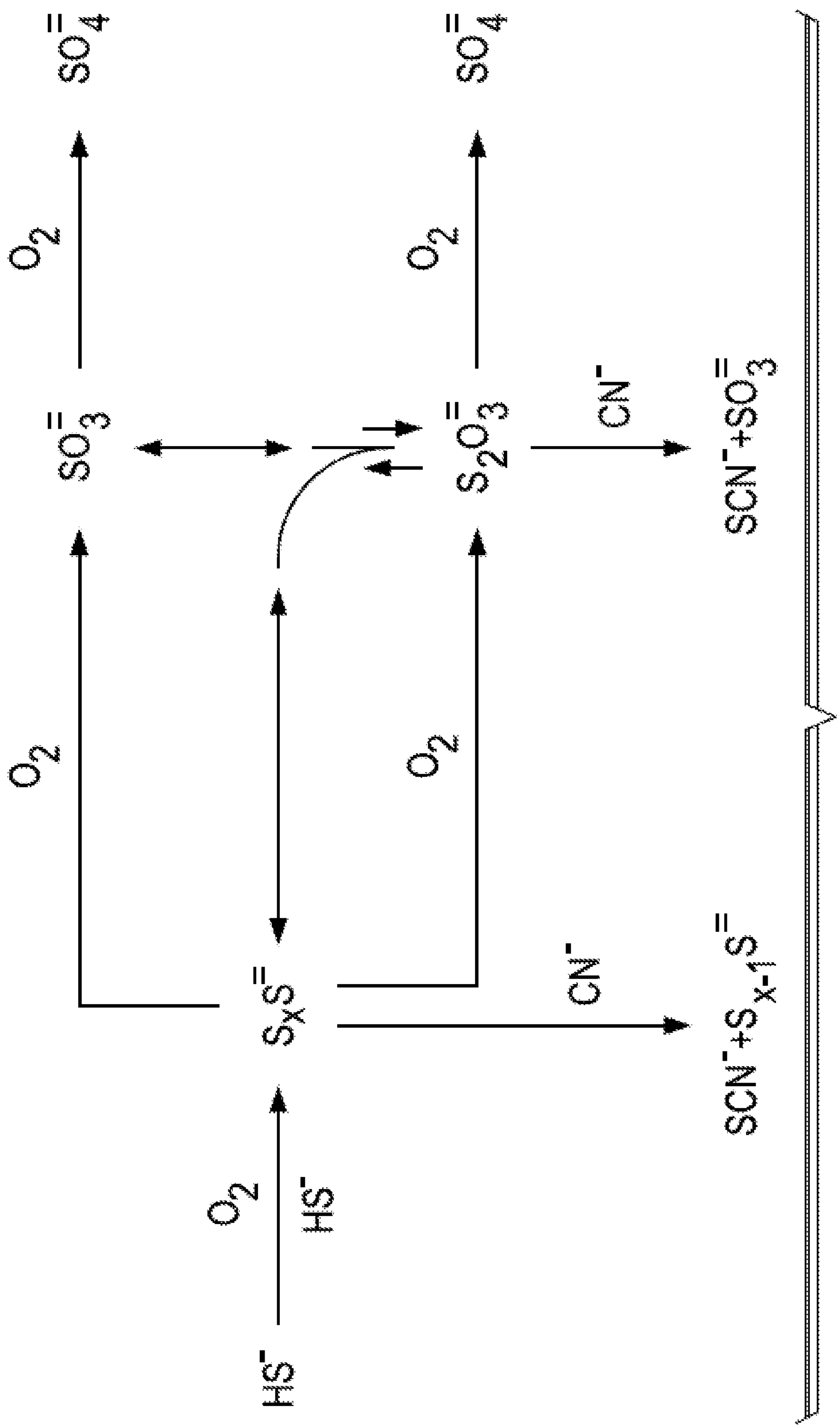
FIG. 5. $H_2S$ and cyanide reaction.
Figure 6:
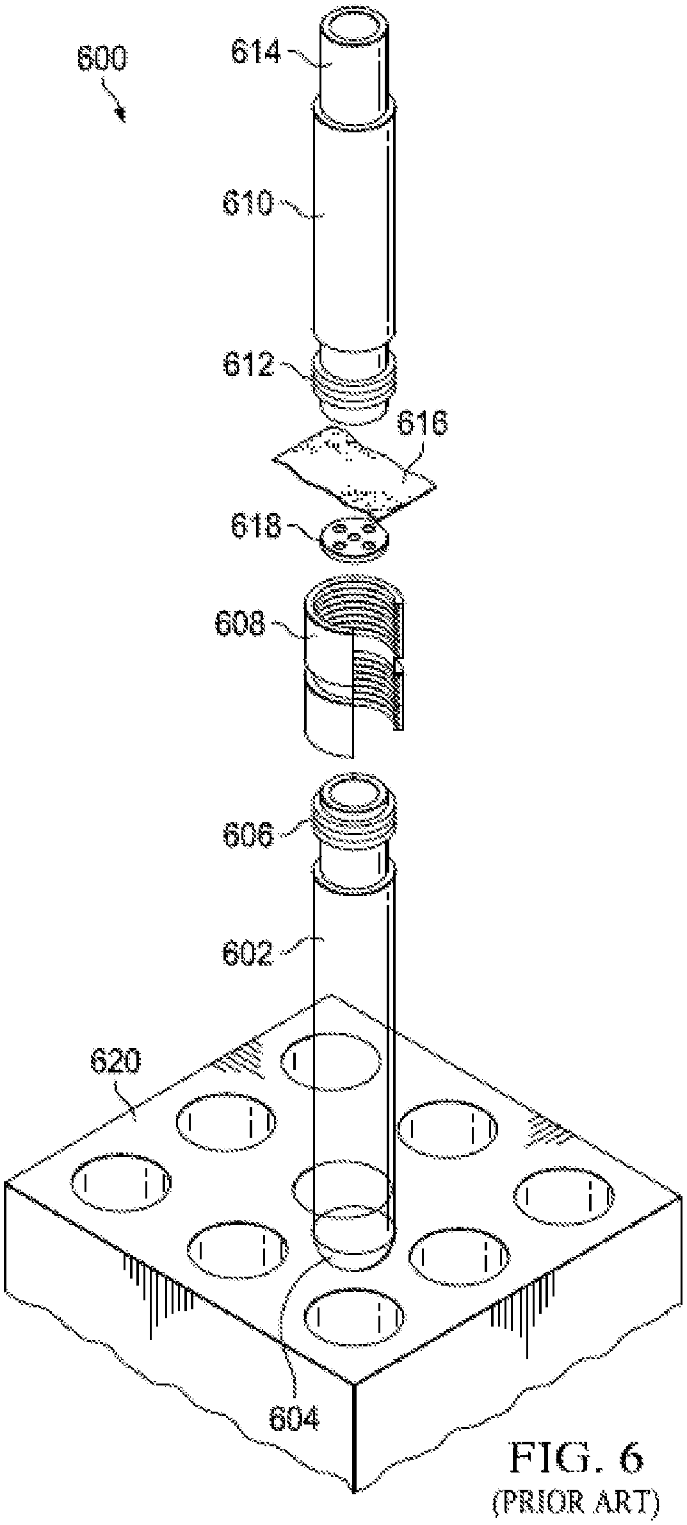
FIG. 6 Prior Art: Exemplary microdistillation device.

In the present disclosure, distillation over caustic cyanide solution is carried out using a micro-distillation apparatus (for example as described in U.S. Pat. No. 5,160,413) to distill elemental sulfur or a-DTZ as $H_2S$. FIG. 6 shows an exemplary micro-distillation apparatus 600 from U.S. Pat. No. 5,160,413 that can be used in the methods. Device 600 consists of a lower elongated distillation column 602, boiling chip 604, threads 606 and 612 and threaded connector 608 serve to connect column 602 to cyanide trapping reservoir/column 610. Teflon support disk 618 and Teflon tape 616 ensure a fluid tight connection. Vent 614 serves to stop the buildup of pressure and thus safe operation of the distillation apparatus. The micro-distillation set-up is placed on heating mantle 620 which can control the temperature.

In general, the distillation in the micro-distillation apparatus is carried out by adding a sample to be analyzed mixed with a reducing mercaptan solution that contains an amine and an alcohol for a-DZT and mercaptans for $S_8$, and optionally a hydrocarbon to maintain viscosity in the lower elongated member of the column 602 (FIG. 6). The sample to be analyzed may be a sample of drilling mud containing a-DTZ, or a sample of crude oil containing unknown amount of elemental sulfur, or other reservoir sample. The cyanide trapping reservoir/column is attached to this lower elongated column of the micro-distillation apparatus before heating the sample in the lower distillation column.

The sample is placed in the lower elongated member of the micro-distillation column and heated to appropriate temperature controlled by the heating mantle. The heating temperature is based on a number of factors including the amount of sample used for distillation, the viscosity of the solution, the specific combination of mercaptan, amine and alcohol used, etc.

Upon reaction with the reductive mercaptan solution, the a-DTZ or the elemental sulfur in the respective samples to be tested releases $H_2S$ gas. Heating for 15-45 minutes vaporizes the $H_2S$ which passes upward from the lower elongated member through a permeable membrane (usually a Teflon tape) into the upper elongated cyanide trapping reservoir/column. This trapping column contains caustic cyanide solution which reacts with the $H_2S$ gas to produce thiocyanate and/or isothiocyanate. These are easily measured by e.g., ion chromatography or colorimetric analysis with iron salts, spectrophotometric analysis, copper-pyridine method, and the like. The amount of elemental sulfur or a-DTZ in the starting sample solution can then be back calculated.

Analysis Method amorphous DTZ: The drilling mud containing a-DTZ to be analyzed is first prepared to remove all impurities and components that may interfere with the reaction of a-DTZ with reductive mercaptan. These interferences must be removed to use $H_2S$ as a proxy for a-DTZ concentration.

This is achieved by a rigorous washing program including washes with weak acids, hydrocarbon, alcohols, and water. The cleaned solids are then added to the lower elongated column of the micro-distillation apparatus followed by the addition of mercaptan, amine and alcohol solution. Optionally a hydrocarbon is also added to this column to maintain the viscosity of the solution so as to allow for uniform heating of the solution. Immediately after the reduction solution is added, the trapping column is attached, and the lower distillation column is heated.

The assembled apparatus is heated for 15-45 minutes to allow all evolved $H_2S$ diffuse across the Teflon tape barrier and react with the caustic cyanide solution resulting in production of thiocyanate or isothiocyanate as shown in Eq. 3. This thiocyanate and/or isothiocyanate is measured by one of the various analytical methods and back calculated to determine the amount of a-DTZ in the original solution. This number can then be added to the number obtained by separately measuring dithiazine and/or $H_2S$ in the samples, providing a more accurate total $H_2S$ reading.

Copper-pyridine thiocyanate analysis method can be used whereby the thiocyanate stoichiometrically reacts with copper(II) salts in the presence of pyridine to form a bright green complex that precipitates and is easily quantified, shown in Eq. 4. A more common method of reaction with iron(III) salts can be carried out that forms bright red iron-thiocyanate complex, shown in Eq 5, which can be analyzed using a spectrophotometer.

$$H_2S + CN^- \xrightarrow{\text{Aqueous + Alkaline}} SCN^-$$

Eq. 3. Reaction of caustic cyanide solution with $H_2S$ to form thiocyanate.

-continued $$2SCN^- + Cu^{2+} \longrightarrow Cu(SCN)_2 \xrightarrow[\text{Pyridine}]{C_2H_5N} Cu(C_2H_5N)_2(SCN)_2$$

Green Precipitate

Eq. 4. Reaction of thiocyanate with copper (II) salt to form copper complex.

$$SCN^- + Fe^{3+} \longrightarrow [Fe(SCN)]^{2+}$$

Red Color

Eq. 5. Reaction of thiocyanate with iron (III) salts to form red complex.

One particular process for the analysis of a-DTZ will involve taking 3.0 g of drilling mud in a 50 mL separation flask followed by the addition of 15 mL n-hexane. Mixing the content of the flask thoroughly and decanting the n-hexane. This n-hexane wash will be carried out 2-3×. Acid wash will be carried out with 2-3× 15 mL wash with dilute hydrochloric acid solution. Water wash with 2-3× 15 mL distilled water will then carried out and the solution centrifuged for 20 minutes to remove water soluble impurities. The resulting drilling mud sample will be air dried at room temperature and weighed and placed in a lower elongated column of the micro-distillation apparatus.

In a measuring flask, 5 mL dithiothreitol or 2-mercaptoethanol, 5 mL N,N-dimethyl-N-(2-hydroxypropyl) amine and 5 mL butanol will be added and mixed with the drilling mud sample. This solution will be slowly poured over the lower elongated column of the micro-distillation apparatus. The $H_2S$ trapping column will be immediately attached to the lower elongated column and the set-up will be placed on a heating mantle. This solution will be heated at 45° C. for 25 minutes. $H_2S$ gas will evolve which will diffuse across the Teflon tape barrier into the trapping column containing known amount of caustic cyanide solution.

After the completion of the reaction, the set-up will be allowed to cool and the trapping column will be removed and treated with standardized solution of ferric ammonium sulfate solution and analyzed by spectrophotometer. The amount of $H_2S$ evolved in the micro-distillation apparatus will be calculated. The amount of a-DTZ in the starting material will be back calculated by knowing this $H_2S$ amount.

Analysis Method Elemental Sulfur: Quantitative analysis of crude oil samples to determine elemental sulfur is carried out by first removing any trapped $H_2S$ gas, entrained water, inorganic sulfides and polysulfides. These chemicals would give a positive bias to the quantification described herein and must be removed, although as above may be separately quantified and contribute to total sulfur levels if desired.

Entrained water can be eliminated by centrifugation. Dissolved $H_2S$ can be removed by sample acidification, dilution, and refluxing. The acidification/dilution solution will reduce sample viscosity and maintain a single-phase solution as the analysis progresses.

The purged, diluted sample is cooled before adding the reduction solution. The reduction solution would contain a reducing agent solution comprising of a mercaptan, an amine, an alcohol and optionally a hydrocarbon. This solution would induce the conversion of elemental sulfur to $H_2S$ and maintain a single phase in the distillation column.

Immediately after the reduction solution is added, the trapping column is attached to capture any evolved $H_2S$. The assembled apparatus would be heated for 15-45 minutes to allow all evolved $H_2S$ diffuse across the Teflon tape barrier and react with the caustic cyanide solution resulting in production of thiocyanate or isothiocyanate. This thiocyanate and/or isothiocyanate would then be measured by one of the various analytical methods discussed above and back calculated to determine the amount of elemental sulfur in the original solution.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description and abstract are not to be used to limit the scope of the invention. The invention is specifically intended to be as broad as the claims below and their equivalents.

Element Sulfur Analysis

A proposed experiment to prove proof of concept is described next:

A. Centrifuge a sample of $S_8$-containing hydrocarbon to settle entrained water;
B. Transfer 1-5 mL centrifuged hydrocarbon in the 602 section of the micro-distillation apparatus;
C. Pipet 1 mL of a 2%-48%-50% valeric acid, isopropanol, toluene solution into section 602;
D. Cover with Teflon membrane and heat to 100-110° C. for 15-45 minutes to remove free $H_2S$ from fluids;
E. Remove section 602 from the heater and cool to below boiling point, then pipet 1 mL of a 1.25%-28.75%-35%-35% triethylamine, 2-mercaptoethanol, isopropanol, toluene solution thereinto;
F. Cap with section 610 and reflux for 15-45 minutes; and
G. Remove caustic cyanide solution and analyze via preferred analytical method for thiocyanate and/or isothiocyanate.

A-Dtz in Drilling Mud Analysis

A proposed experiment to prove proof of concept is described next:

A. Isolate drilling solids using centrifugation or filtering apparatus;
B. Wash solids with hot xylenes 3× to remove hydrocarbons and elemental sulfur from the solids;
C. Wash solids 3× with methanol and 3× with water to remove remaining dissolvable material;
D. Dry remaining solid in vacuum overnight;
E. Transfer 100-1000 mg dried solids to section 602;
F. Pipet 1 mL of a 2%-48%-50% valeric acid, isopropanol, toluene solution into section 602;
G. Cover with Teflon membrane and heat to 100-110° C. for 15-45 minutes to remove free $H_2S$ from fluids;
H. Remove section 602 from heater and cool below boiling point, then pipet 1 mL of a 1.25%-28.75%-35%-35% triethylamine, 2-mercaptoethanol, isopropanol, toluene solution;
I. Cap with section 610 and reflux for 15-45 minutes; and
J. Remove caustic cyanide solution and analyze via preferred analytical method for thiocyanate and/or isothiocyanate.

The following references are incorporated by reference in their entirety.

U.S. Pat. No. 5,160,413 Micro-distillation process for cyanide.
US2012247515 Methods for dissolution of amorphous dithiazine.
US2013149788 Assay for quantifying elemental sulfur levels in a sample.
Ser. No. 17/494,673 (US20220112443) Method for dissolution of amorphous dithiazines.
Ser. No. 17/494,470 (US20220112433) Elemental sulfur dissolution and solvation.
Grahame T. N.; Matherly, R. "Use of Portable Analytical Methods to Determine the Stoichiometry of Reaction for Hexahydrotriazine-Based Hydrogen Sulfide Scavenger Operations." Anal. Chem. 86(10): 4879-4882 (2014).
Saleh, T. A. "Characterization, determination and elimination technologies for sulfur from petroleum: Toward cleaner fuel and a safe environment." Trends in Environmental Anal. Chem., 25: e00080 (2020).
Long, J. H. "A textbook of elementary analytical chemistry qualitative and volumetric." (1910)

The invention claimed is:

1. A method of producing oil, said method comprising:

a) obtaining a plurality of samples, each sample from a known location in an oil reservoir and containing MEA or a triazine, or MEA or a triazine being added thereto;
b) optionally analyzing each of said plurality of samples or portion thereof to determine a first amount of $H_2S$ remaining unreacted with said MEA or triazine after step a);
c) analyzing each of said plurality of samples or portion thereof to determine an amount of dithiazine and correlating said amount of dithiazine to a second amount of $H_2S$;
d) analyzing each of said plurality of samples or portion thereof for an amount of amorphous dithiazine (a-DTZ) by treatment with a reductive mercaptan solution to convert a-DZT to $H_2S$ and measuring a third amount of $H_2S$ and correlating said third amount of $H_2S$ to said amount of a-DTZ in said plurality of samples;
e) calculating a total amount of $H_2S$ in a each sample from a each said known location by adding said optional first amount of $H_2S$ from step b), said second amount of $H_2S$ from step c), and said third amount of $H_2S$ from step d), thereby determining one or more highest $H_2S$ content location(s) in said reservoir and one or more sweeter content location(s);
f) producing oil from said one or more sweeter content location(s) as determined in step e); and
g) wherein said produced oil has less $H_2S$ than a method of producing oil from said reservoir without steps a) through f).

2. The method of claim 1, wherein plurality of samples are drilling mud samples obtained while drilling an oil well or a test well.

3. The method of claim 1, wherein said plurality of samples are core samples.

4. The method of claim 1, wherein said reductive mercaptan solution comprises a mercaptan, an amine and an alcohol.

5. The method of claim 1, wherein said optional first, said second, and said third amounts of $H_2S$ are measured by a reaction with caustic cyanide and determining an amount of thiocyanate or isothiocyanate produced.

6. The method of claim 5, wherein said amount of thiocyanate or isothiocyanate is determined by reaction with iron or copper plus pyridine and measuring an amount of color produced.

* * * * *